United States Patent [19]
Horibata

[11] Patent Number: 5,752,329
[45] Date of Patent: May 19, 1998

[54] WALKING AND HOPPING SHOE WITH A MASSAGING SOLE SURFACE

[76] Inventor: Hiroshi Horibata, Mitaka House No. 25-20, 5-chome, Kamirenjaku, Mitaka-shi, Tokyo, 181, Japan

[21] Appl. No.: 675,613

[22] Filed: Jul. 3, 1996

[30] Foreign Application Priority Data

Jul. 5, 1995 [JP] Japan ................. 7-008282 U

[51] Int. Cl.$^6$ ............... A43B 13/28; A43B 3/10; A61F 5/14
[52] U.S. Cl. ................. 036/27; 36/141; 36/7.8
[58] Field of Search ................. 36/11.5, 43, 44, 36/141, 27, 37, 7.8

[56] References Cited

U.S. PATENT DOCUMENTS 4,109,661  8/1978  Fukuoka ................. 36/141
4,457,084  7/1984  Horibata et al. ................. 36/28 X

FOREIGN PATENT DOCUMENTS

1771732  10/1988  Japan.
H414005  3/1992  Japan.
H8-4042  2/1996  Japan.

*Primary Examiner*—B. Dayoan

[57] ABSTRACT

An improved walking and hopping shoe comprises a shoe body having at least a detachable soft stimulating piece of a stimulating and deodorizing double insole on an inside bottom of the shoe body, a pair of the same or different coil springs, and a double elastic uneven base plate connected with the springs through the sole of the shoe body. The stimulating piece or insole applies pressure to selected points on the sole of the foot. The deodorizing insole electrolytically functions to generate oxygen to sterilize and to prevent odors inside the shoe body. The shoe provides a safe and health sport and which permits recovery from human fatigue or slight illness as a result of walking or hopping.

19 Claims, 6 Drawing Sheets

WALKING AND HOPPING SHOE WITH A MASSAGING SOLE SURFACE

This invention relates to a walking and hopping shoe and more particularly to a walking and hopping shoe which can smoothly walk and hop by providing therein selected coil springs having a dimension and configuration that is the same as that of a special elastic base plate, and which permits rapid recovery of human fatigue or a human slight illness, as a result of the improvement of the circulation of the blood and lymph by stimulating a selected TSUBO point which connects with the autonomic nervous system on the sole of the foot by at least a soft stimulating piece or a stimulating and deodorizing double insole attached on the inside bottom of the sole, during the walking or hopping movements.

The present inventor has previously suggested a hopping shoe comprising a sports shoe, a pair of coil springs and an elastic base plate wherein those parts are connected respectively with a connecting means, such as a bolt-nut set, to contribute to shape-up or build-up of the body by walking, hopping, dancing or jogging, as disclosed in U.S. Pat. No. 4,457,084 and Japanese Utility Model Registration No. 1,771,732.

Such a known hopping shoe could attain the desired end for the present invention; however, in the case of violent movement, such a jogging, etc., the repelling action of the coil springs thereof was not always sufficient and was slightly imperfect in functionally absorbing equally a shock or pressure on an ankle.

It was found, however, that such insufficient repelling action during violent hopping or jogging movement is overcome by selecting proportionally a configuration and/or dimension of the coil spring in accordance with a distribution and strength of the shock or stress added on the coil springs.

In addition, there is no hopping shoe wherein the shoe body provides at least a stimulating and deodorizing insole attached to the inside bottom of the shoe to permit recovery of human fatigue or human slight illness by stimulating strongly the sole of a foot during walking or jogging.

SUMMARY OF THE INVENTION

An improved walking and hopping shoe comprises a shoe body provided with at least a stimulating piece or a stimulating and deodorizing insole attached to the inside bottom of the shoe, a pair of coil springs having selected dimensions and/or configurations, in accordance with the distribution and strength of the shock or stress added on the coil springs, and an elastic rather hard base plate covered with an elastic skid-proof rather soft plate, and which is used for recovery of a human fatigue or slight illness by stimulating the TSUBO points on the sole of a foot during walking, jogging, hopping, or dancing.

In oriental medicine, the sole of the foot is considered as a so-called second heart because there are many TSUBO points (KEIKETSU) which are, respectively, a vital part of the autonomic nervous system and for which physiotherapy stimulates the respective TSUBO point by finger pressure. This technique has been introduced generally to permit recovery of human fatigue or slight illness.

Accordingly, the present walking and hopping shoe is provided with a stimulating piece or stimulating and deodorizing insole to excite selected TSUBO points during walking or hopping by the weight of the wearer so that human fatigue or slight illness can have remarkable recovery.

The stimulating piece comprises a hummer type screw or a mushroom type screw, in cross-section, covered with a soft material on a head portion, and attached detachably by a nut on a selected portion of an inside bottom of the shoe, through only the sole or within the insole.

The stimulating and deodorizing insole may also be used for the same purpose as the stimulating piece, and consists of an insole in which a primary insole is piled with a bond on a secondary porous insole or both insoles are attached slightly on an inside sole or the shoe body by means of a screw tightening means, such as a bolt and nut set, together with an upper most coil spring piece to also be outwardly attached.

The primary insole is also made from a soft porous material and is provided with various projections to excite by the weight of the wearer TSUBO points on the sole of the foot as to permit recovery of human fatigue and slight illness during walking, hopping or jogging.

The secondary porous insole, which can be slightly penetrated into between different front and rear metallic washers and bolt heads, which attaches outwardly the upper most coil spring on the sole of the shoe body. The secondary insole forms a certain cell by ionization of the different metals into a secreting fluid, such as sweat, when it is wetted by the fluid and generates activated oxygen and chlorine from a surface of the electrodes formed by the different metals by decomposition of the secreting fluid which forms an electrolyte when both electrodes are electrically connected to a conductor, such as a wetted second insole or wetted sole of a foot.

Consequently, the activated oxygen and chlorine sterilizes the insole and the foot to prevent formation of athlete's foot, and decomposes a bad smell component of the secreting fluid to deodorize the inside of the shoe.

The best dimension and/or configuration of the coil springs for the walking and hopping shoe may be selected in accordance with the strength of the shock or stress added on the coil springs so as to absorb smoothly the shock or stress and to strongly repel effectively as possible, during walking or hopping.

An elastic base plate for the hopping shoe comprises a laminated plate of rubber or laminated plastics which is a rather soft elastic plate having an uneven outer surface on a rather hard elastic base plate for the purposes of skid-proof and sound-proof in a room or studio, etc.

It is an object of the present invention to provide an improved walking and hopping shoe which enables smooth hopping and walking.

It is another object of the present invention to provide a healthy walking and hopping shoe to recover human fatigue and slight illness by stimulating the selected TSUBO point on the sole of the foot with a stimulating piece or a stimulating and deodorizing insole, during hopping, walking or jogging.

It is another object of the present invention to provide a healthy and sanitary walking and hopping shoe to deodorize the inside shoe body by ionic decomposition of secreting fluid from activated gas generated from the different metals on the inside bottom of the shoe body.

It is further object of the present invention to provide a healthy and sanitary walking and hopping shoe to prevent generation of athlete's foot by sterilization of the inside shoe body with activated gas generated from different metals on the inside bottom of the shoe body.

It is still further an object of the present invention to provide a safe and sound-proof walking and hopping shoe

DETAILED DESCRIPTION OF THE PREFERRED EMBODIMENTS

Figure 1:
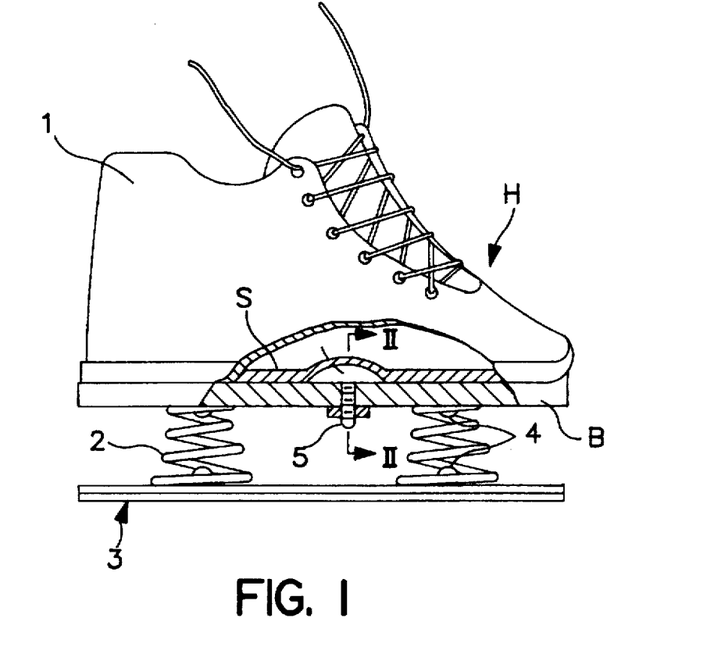
FIG. 1 is a partial sectional front side view of an improved walking and hopping shoe.
Figure 2:
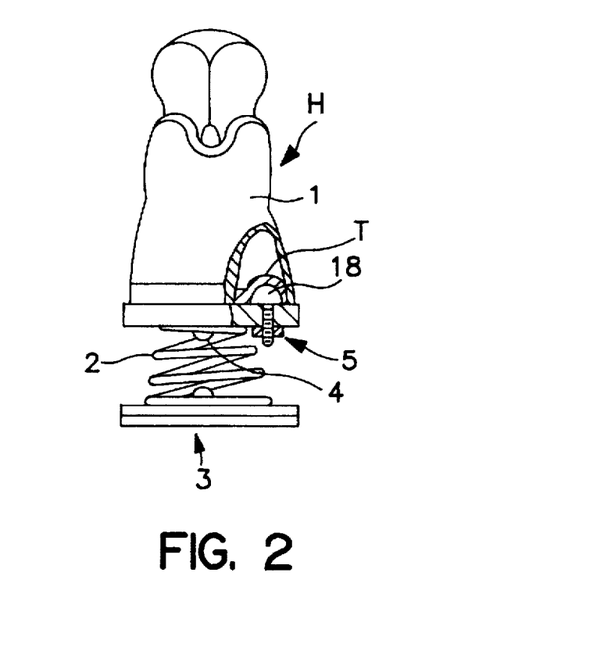
FIG. 2 is a partial sectional rear view of the improved shoe.

Referring to the drawings and particularly FIG. 1 and FIG. 2, an improved walking and hopping shoe H comprises mainly a shoe body 1, a pair of coil springs 2, and an elastic base plate 3 covered with a rather soft uneven elastic plate 7. The shoe body 1 is connected with the elastic base plate 3 through the pair of coil springs 2 by means of bolts and nuts 4 at their upper and lower ends, respectively.

The improved shoe is also provided detachably with at least a stimulating piece 5, between an insole S and a sole B of the shoe body 1, through the later at a selected portion or portions corresponding to approximately a desirable TSUBO point "YUSEN" shown as T in FIGS. 2 and 6 which is in the plantar arch, etc.

Figure 5:
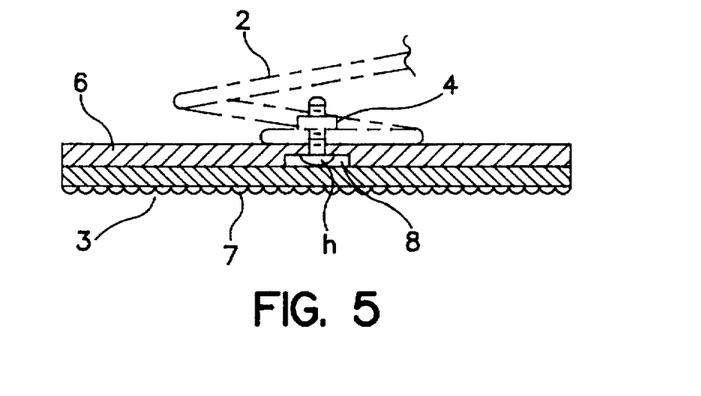
FIG. 5 is an enlarged sectional view of an elastic base plate for the improved shoe.

The coil springs 2 are attached to the elastic base plate 3 in various combinations of the various dimensions and/or configurations, as described hereinafter, and the elastic base plate 3 is formed into a combined elastic plate from a rather hard elastic plate 6 and a rather soft uneven elastic plate 7, with a suitable adhesive material, so that the later prevents slippage on the ground and exposure to a head h' of the bolt 4 in a cavity 8, as shown in FIG. 5.

Figure 3:
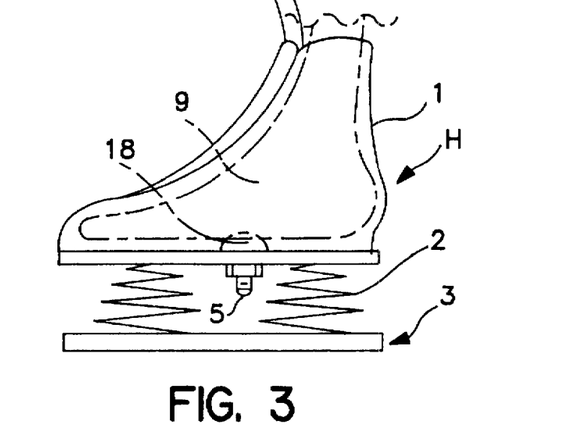
FIG. 3 is a side view of the improved shoe.
Figure 9A:
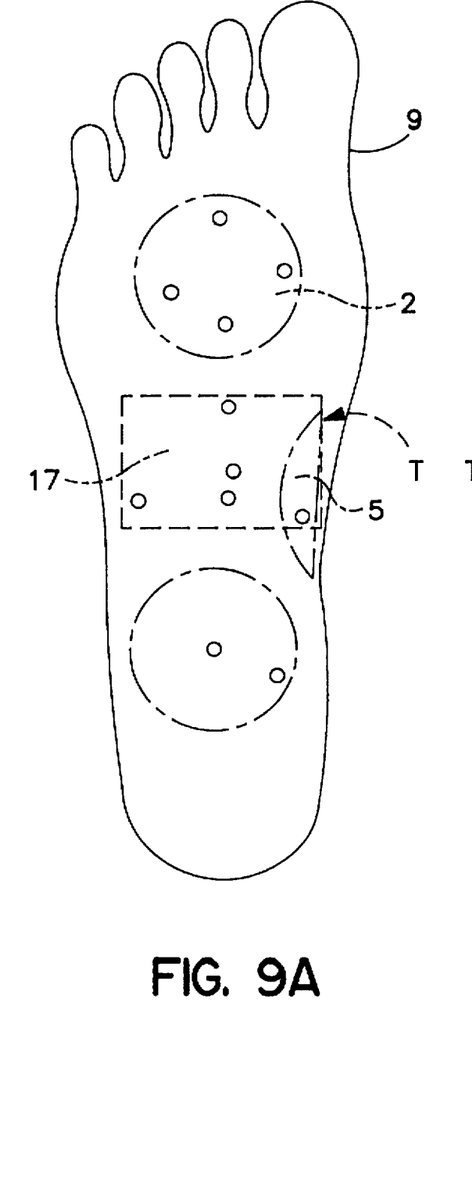
FIGS. 9(A) and 9(B) are planar side views showing main TSUBO points on the soles of a left and right foot.
Figure 9B:
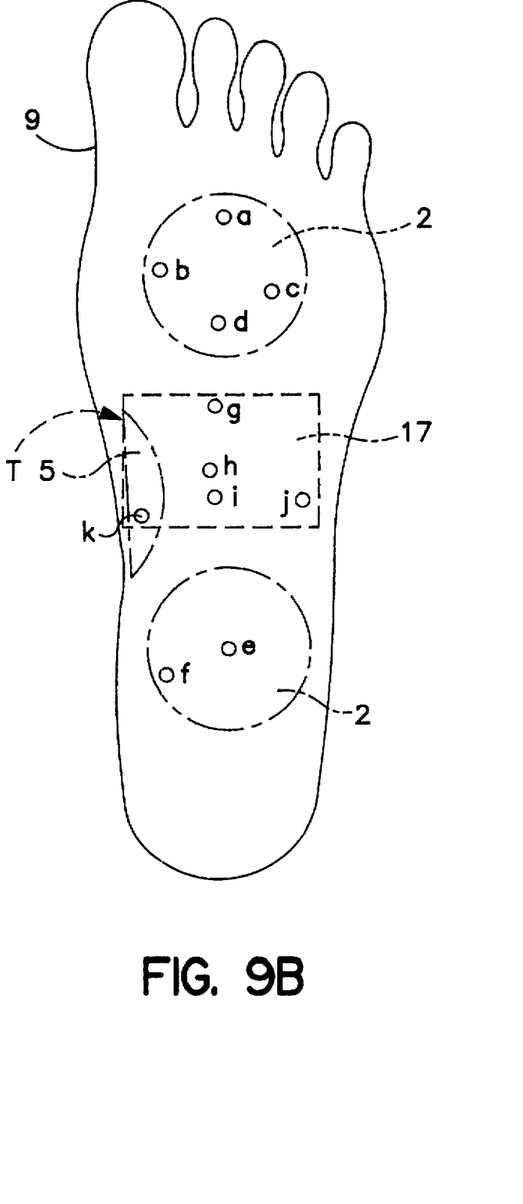

FIG. 3 shows one embodiment of the present improved shoe H which comprises a high cut shoe body 1 provided with a detachable stimulating piece through the shoe, a pair of helical coil springs 2 of the same dimension and the same configuration, and a combined elastic base plate 3, as described hereinbefore. In such a shoe H the position of the stimulating piece 5 may be relocated to another selected position on the sole of the shoe body 1, such as from k to h as shown in FIG. 9, in accordance with a condition of fatigue or slight illness. The head 18 of the stimulating piece 5 pushes continuously on the selected TSUBO point k or h, during walking or hopping, to arrange an unstable condition of disturbance of the autonomic nervous system on which the selected TSUBO point belongs and consequently a wearer of the shoe overcomes the human fatigue or slight illness.

Figure 4A:
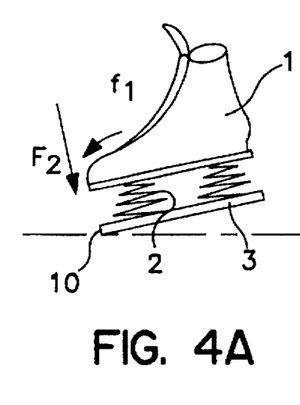
FIGS. 4(A), 4(B), and 4(C) are sequential views showing movements of a wearer's physique and the strength of shock and stress upon landing of the improved shoe.
Figure 4B:
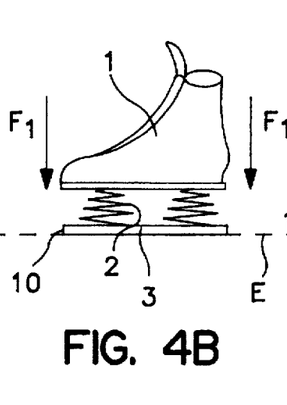
Figure 4C:
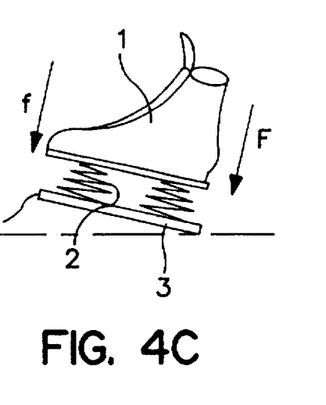

In use, as shown in FIGS. 4(A), 4(B), and 4(C), the wearer of the shoe 1 during walking or hopping firstly steps down a heel portion very strongly along a larger arrow direction F, and then next steps forwardly a front edge portion 10 of the elastic base plate 3, through a toe portion, along a small arrow direction f, as shown in FIG. 4(c). The shoe H, at this moment, is held horizontally as shown in FIG. 4(B) in accordance with the arrows direction F and thereafter the toe portion is forwardly inclined, due to a forward movement of the wearer, as shown in FIG. 4(A) along a small arrow direction $f_1$ to kick at the front edge portion 10.

The kick action at the front edge 10 of the elastic base plate 3 thrusts the wearer forwardly and adds on the front coil springs 2 a rather large stress, along an arrow direction $F_2$, at the same time. The stresses F and $F_2$ on the elastic base plate 3 are not so uniform in their strength, respectively, so that the dimension and/or configuration of the coil springs 2 may be selected in accordance with the stress added thereon.

In this continuous replacement of the wearer's weight (the center of gravity of the wearer), the stress F on the rear coil spring is more stronger that the stress $F_2$ upon the kick motion on the front coil spring, and therefore, it is preferable that the rear coil spring has more stronger repel than the front spring to maintain smooth walking, hopping, or jogging.

Figure 6:
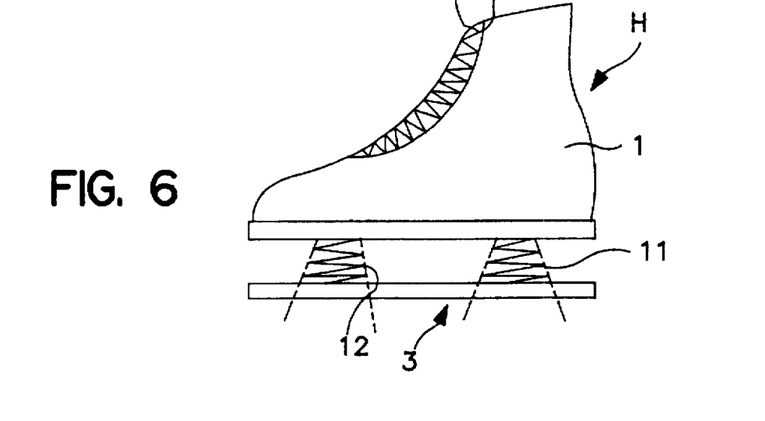
FIG. 6 is a side view of an embodiment for the improved shoe.

Accordingly, the shoe H in FIG. 6 is provided with a pair of helical coil springs 11 and 12 between the shoe body 1 and the elastic base plate 3 and both springs are respectively of the same configuration but a wire dimension of the rear spring is larger than that of the front spring.

Figure 7:
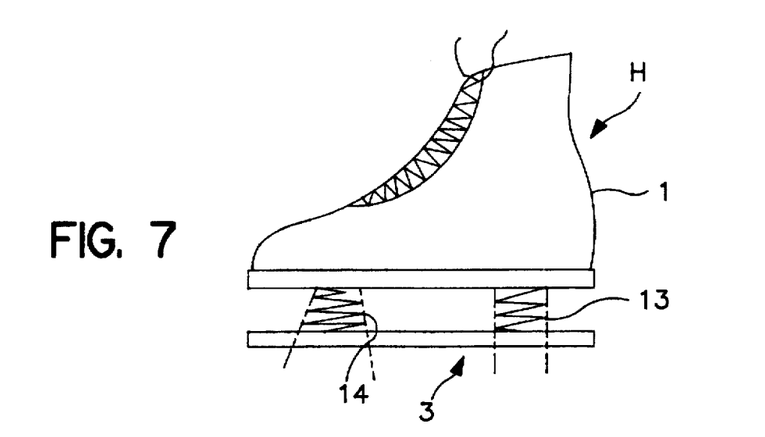
FIG. 7 is a side view of another embodiment for the improved shoe.

The shoe H in FIG. 7 is also provided with a pair of coil springs in which the front coil spring 14 is a helical type spring and the rear coil spring is a cylindrical coil spring 13, and both are of the same wire dimension, respectively.

Figure 8:
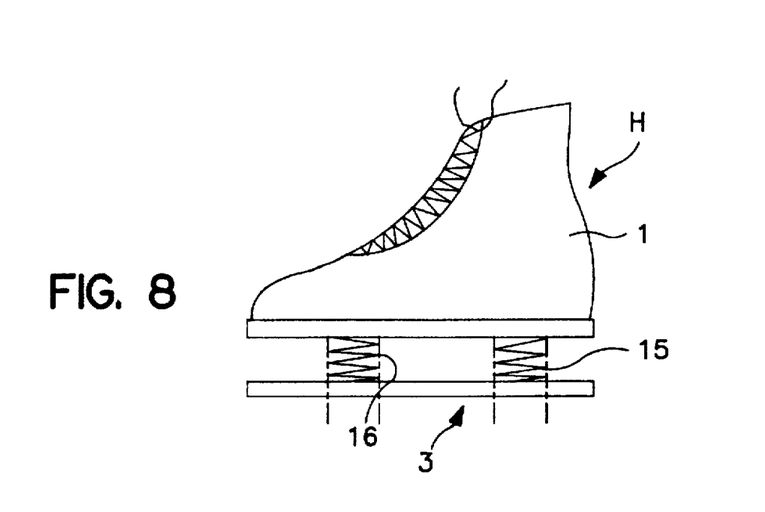
FIG. 8 is a side view of another embodiment for the improved shoe.

The shoe H in FIG. 8 is provided with a pair of cylindrical coil springs 15 in which the configuration is the same by a wire dimension of the rear coil spring 15 is larger than a wire dimension of the front spring, respectively. The different combinations of the coil springs in FIGS. 6 to 8, are effective for smooth walking or hopping, as mentioned before.

The coil springs 2 and the stimulating piece 5 are attached to contact indirectly or directly with the sole of a foot 9 as shown in FIGS. 9(A) and 9(B), and press the many TSUBO positions a, b, c, d, e and f by the wearer's weight, during walking or jogging.

The TSUBO positions connect, respectively, with the autonomic nervous system, and controls or recovers the human fatigue or slight illness by stimulating thereof.

In an area 17 between the coil springs 2, there are also so many important TSUBO points g, h, i, j and k that another detachable stimulating piece 5 as shown in FIGS. 10 to 14, may be attached to stimulate directly in a suitable position in this area. It has also been reported in oriental medicine that the stimulation of those TSUBO points by finger pressure, moxa cautery, acupuncture, etc., is good for the recovery of human fatigue or slight illness and their treatments have been applied magnificently not only in the medical world but also in the sporting world, etc.

The TSUBO point shown on the sole of a foot 9 in FIGS. 9(A) and 9(B) relate, respectively, to an internal organ through "KEIRAKU" (the autonomic nervous system), and the former is activated with the later by stimulating the selected TSUBO point for recovery.

The following table shows a mutual relation between the TSUBO point to be stimulated by the hopping action, etc., and the internal organ to be recovered by stimulation.

| TSUBO Point to be Stimulated | Internal Organ or Illness to be Activated or Cured |
| --- | --- |
| a | The lungs and the bronchus |
| b | The gall bladder |
| c | The heart |
| d | Hypotension disease |
| e | The adrenal bodies |
| f | The sciatic nerve |
| g | The adrenal bodies |
| h | The heart and kidney |
| i | The intestines |
| j | The large intestines |
| k | The back bone, hypotension |

Figure 10A:
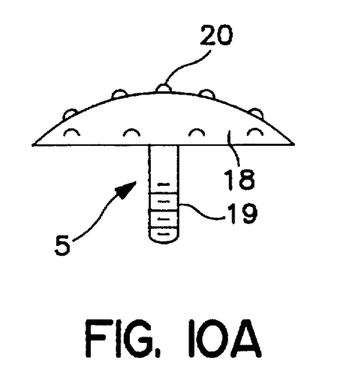
FIGS. 10(A) and 10(B) are front and side views of a stimulating piece for the sole of a foot in the improved shoe.
Figure 10B:
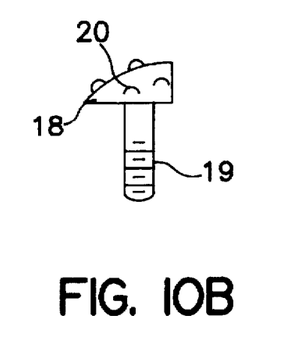
Figure 11:
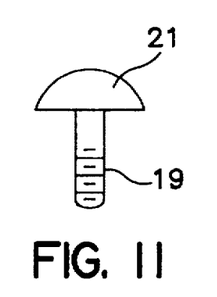
FIG. 11 is a front view of another embodiment of the stimulating piece of FIGS. 10(A) and 10(B).
Figure 12A:
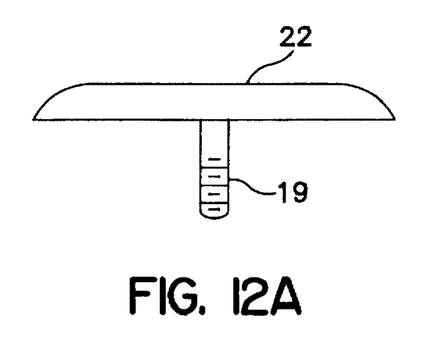
FIGS. 12(A) and 12(B) are front and side views of another embodiment of the stimulating piece of FIG. 10(A) and 10(B).
Figure 12B:
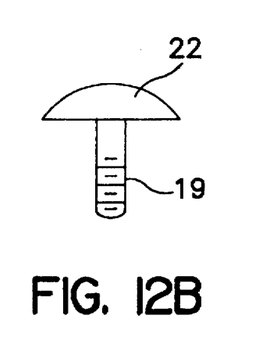

The important TSUBO points a–f described hereinbefore are included with the areas of the front and rear coil springs 2 and stimulated indirectly by the upper most coil spring pieces, through the sole of the shoe body, during walking, hopping, etc.; however, the other TSUBO points g–j in the central area 17 between the coil springs 2, as mentioned above, may be stimulated directly with another stimulating piece 5 as shown in FIGS. 10–12, especially in FIG. 12, which is provided with a long curved head, such as a pillow 22, and is attached detachably on a bottom of the shoe body 1 by a screw 19 and nut as shown in FIG. 3.

The curved heads 18, 21 and 22 of the stimulating pieces 5 may be covered with a thick soft layer such as a plastic material so that the sole of a foot is stimulated comfortably without any pain and any ache, through walking, hopping, jogging, etc., respectively.

The curved heads may also be provided with many projections 20 on their surfaces and formed into various configurations such as rivet type, or a hoe or hammer type, a pillow type, etc.

The single or multiple of such stimulating piece or pieces 5 may of course, be used in any areas on the inside bottom of the shoe body 1, except for the areas corresponding to the upper most spring pieces, and a magnetic stimulating piece and the like may also be used for them.

Figure 13:
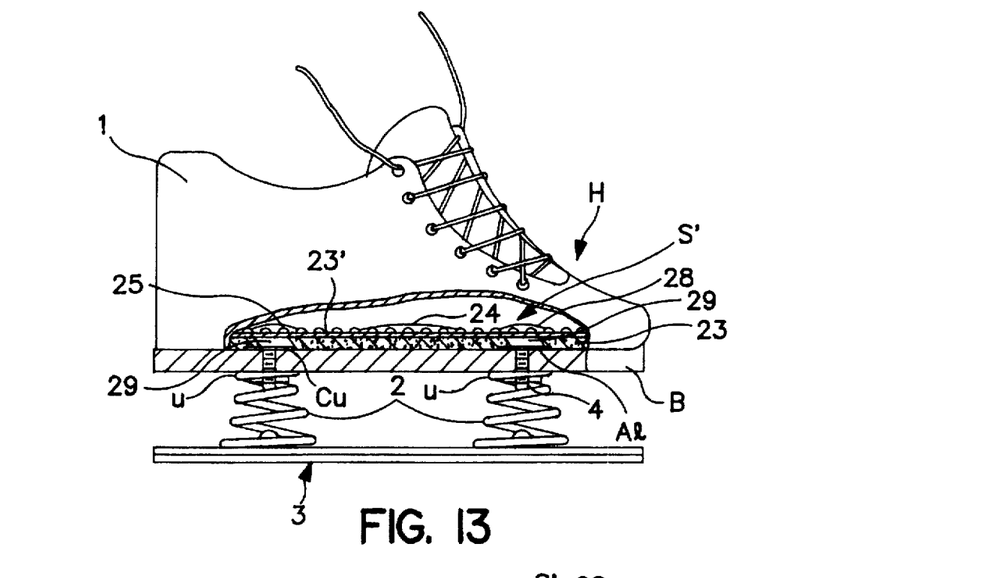
FIG. 13 is a partial sectional side view of another embodiment of the improved shoe provided with a stimulating and deodorizing insole.

The shoe H shown in FIG. 13 is another embodiment of the present invention, and is provided with a stimulating and deodorizing insole S' which is effective not only to stimulate the sole of a foot but also to deodorize and sterilize inside the shoe body.

The insole S' comprises a porous soft lower insole 23 and an uneven porous soft upper sole 23'.

The lower insole 23 may cover a bolt head 29 or may be slightly penetrated by the bolt head 29 and be adhered with the upper insole 23' by a plastic bond.

Figures 14A, 14B, 15:
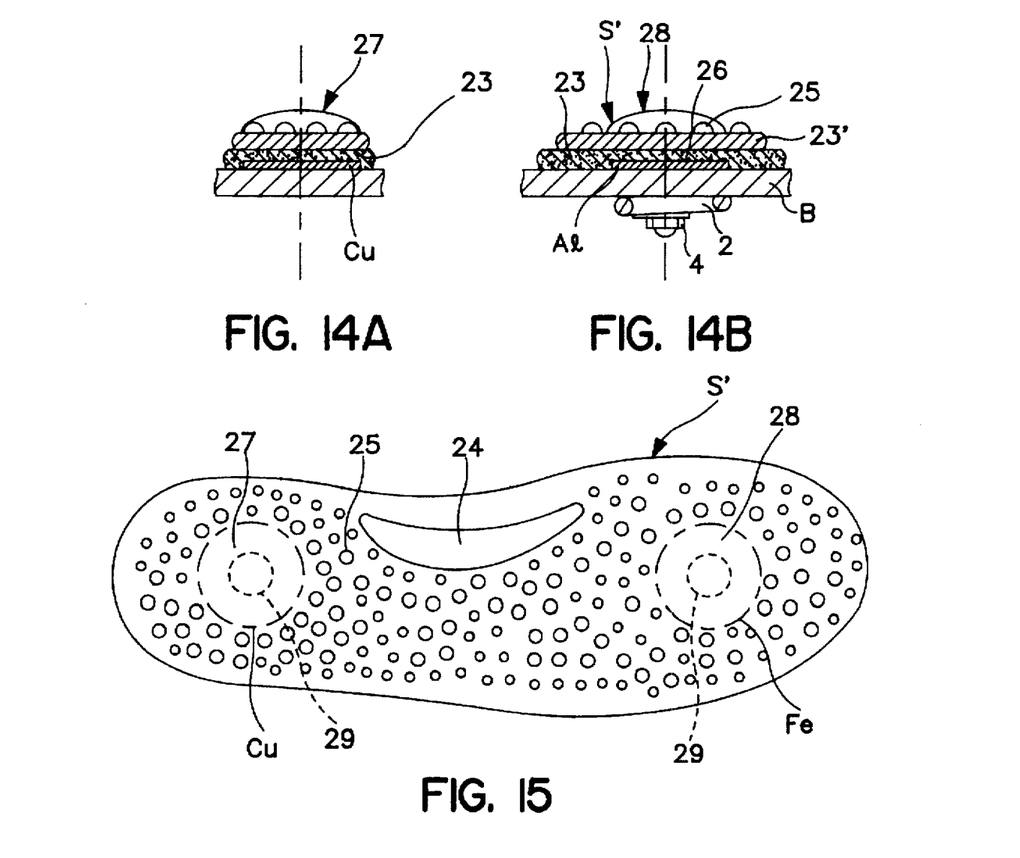
FIGS. 14(A) and 14(B) are enlarged sectional views, respectively, of a sole and insole of the improved shoe.
FIG. 15 is a plan bottom view of the stimulating and deodorizing insole.

As shown in FIGS. 14(A) and 14(B), a surface of the upper insole 23' is also provided with many small projections 25, front and rear large curved projections 27 and 28 and a crescent shaped projection 24 in a portion of the plantar arch, respectively, so that they can stimulate suitably the TSUBO points on the sole of a foot, by empty weight of the wearer.

The size and density of the small projections on the upper insole 23' are decided in accordance with the density of the TSUBO points on the sole of a foot, as shown in FIGS. 9(A) and 9B).

The large curved projections 27 and 28 are arranged at the positions corresponding to the bolt heads 29 and in the same area as the metallic washers 26 for the bolts 4 described hereinafter. The crescent shaped projection 24 is also arranged on a portion of the plantar arch on the upper insole 23' in a form inwardly inclined along an inside wall of the shoe body 1.

Accordingly, the TSUBO points a–f in the areas 2a corresponding to the upper coil spring pieces in FIGS. 9(A) and 9B) are stimulated by the front and rear large curved projections 27 and 28, which is similar to surfaces of the washers 26, respectively, the TSUBO point k, by the crescent shaped projection 24, and the TSUBO points g–j, by the densed small projections 25.

The metallic washers 26 with the bolt heads 29, as shown in FIGS. 13, 14(A) and 14(B), are covered by the stimulating and deodorizing insole S', after the coil springs 2 with the elastic base plate 3 are attached under the sole B of the shoe body 1, so that the bolt heads 29 and the metallic washers 26 can stimulate suitably the TSUBO points on the sole of a foot within the areas corresponding to the surface of the large curved projections 28, by reverse pressure from the upper most coil spring pieces u, that is to say, from the washer 26 and the head of the bolt 29 added through the sole of the shoe body 1.

The metallic washer 26 and bolt 4 may, respectively, be iron, but the former is preferably a metal such as Cu, Al, etc., which has a stronger ionizing tendency and the same size as the large curved projections 27 and 28.

Such metals, Cu, Al, Fe, etc., dissolve into a solution to generate Cu ions, Al ions, Fe ion, etc., in the solution and electromotive force $\alpha$ produced between such metals in the solution.

The electromotive force $\alpha$ generates an electric current from a positive electrode to a negative electrode if both electrodes are connected with an electric conductor.

In FIGS. 13, 14(A) and 14(B), the front and rear washers 26 may be made of copper (Cu) and/or aluminum (Al) and the bolts 4 may be made of iron (Fe), but the former may be Fe, the later, Cu and/or Al. The front washer of Al and the rear washer of Cu with the head of bolts of Fe covered with the double soft porous insole S' is, respectively, ionized into a solution, such a sweat, containing salt and ammonium components, etc., which are discharged from the sole of the foot, when the porous soft lower insole 23 is wetted by sweat.

Generally, an electromotive force is generated between two metals such as Cu and Al or Fe and Cu in electrolyte solution, each of which has different electrolytic solution tendency, respectively, and electric current flows to a negative electrode from a positive electrode if both electrodes are connected with a conductor, and oxygen releases from the positive electrode.

In the present shoe H, the sweat from the sole of a foot firstly wets the porous soft lower insole 23 through the uneven porous soft upper insole 23' and moisturizes the lower portion of the former.

The front and rear washer 26 moisturizes the lower insole 23 to release a Cu ion and an Al ion due to ionization and the head of the bolt 29, an Fe ion. The electric current generated between the front and rear bolts 29 through the electrolyte solution, such as sweat, in accordance with the electromotive force of the metallic ions, if both bolts 29 or the washers 26 are connected with the wetted uneven porous soft upper insole 23', and releases activated oxygen from a positive electrode; in other words, the rear copper washer, by means of the electrolysis of the sweat moisture.

Thus, the released oxygen sterilizes the inside of the shoe body 1 to protect the skin from a water insect and the electrolysis of sweat solution prevents generation of a bad smell therefrom.

While there has been described and pointed out the fundamental novel features of the invention as applied to preferred embodiments, it will be understood that various omission and substitutions and changes in the form and details of the shoe illustrated may be made by those skilled in the art, without departing from the spirit of the invention. The invention, therefore, is limited only as indicated by the scope of the following claims.

I claim:

1. A walking and hopping shoe comprising:

a shoe body having a sole portion;

an elastic base plate;

front and rear coil springs attached to the body and between the body and the elastic base plate wherein the front coil spring is adjacent a toe portion of the shoe body;

the coil springs comprising a pair of springs connecting the shoe body with the elastic plate by first fastening means;

detachable stimulating means having at least one stimulating projection for engagement with desired TSUBO points on the sole of a foot inserted into the shoe body, the stimulating means comprising a second fastening means including a curved head which may be positioned as desired on an inside bottom of the sole portion of the shoe body;

the elastic base plate comprising a double layer plate formed by a relatively soft elastic plate having an uneven surface adhered to and under a relatively hard elastic plate.

2. The shoe of claim 1 wherein the curved head includes a plurality of projections therefrom.

3. The shoe of claim 1 wherein the pair of coil springs is a combination of springs of the same dimension and configuration.

4. The shoe of claim 1 wherein the pair of coil springs is a combination of springs of different dimension.

5. The shoe of claim 1 wherein the pair of coil springs is a combination of springs of different configuration.

6. The shoe of claim 4 wherein a wire dimension of the front coil spring is smaller than a wire dimension of the rear coil spring.

7. The shoe of claim 5 wherein the front coil spring is a helical coil spring.

8. The shoe of claim 1 wherein the first fastening means comprises at least one pair of mechanical fasteners.

9. The shoe of claim 1 wherein the first fastening means includes a washer having a diameter substantially equal to a diameter of the coil spring at the attachment to the shoe body.

10. The shoe of claim 1 wherein the stimulating means further comprises a soft insole having an uneven surface.

11. The shoe of claim 10 wherein the soft insole comprises porous upper and lower insoles and the uneven surface is on the upper insole.

12. The shoe of claim 11 wherein the second fastening means further includes a bolt head which is urged into the porous lower insole.

13. The shoe of claim 11 wherein the soft insole is removable from the shoe body.

14. The shoe of claim 11 wherein the upper insole has a plurality of curved soft projections at a toe portion and at a heel portion corresponding to a first area formed by washers for the respective front and rear coil springs, a crescent shaped projection in a portion corresponding to a plantar arch, and projections at a second area.

15. The shoe of claim 14 wherein the front and rear washers occupy the same area on the inside bottom of the shoe body which corresponds to positions of the coil springs at their attachment to the body.

16. The shoe of claim 9 wherein each of the coil springs has a respective washer made from a material which releases a metallic ion in a fluid solution.

17. The shoe of claim 9 wherein each of the coil springs has a respective washer formed of a metal having a different ionization tendency.

18. The shoe of claim 16 wherein the metal of the washer is selected from a group consisting of copper, aluminum and iron.

19. The shoe of claim 16 wherein the metallic ion electrolytically reacts with the fluid solution to produce oxygen.

* * * * *